United States Patent [19]

Yager

[11] Patent Number: 5,230,785
[45] Date of Patent: Jul. 27, 1993

[54] METHOD AND APPARATUS FOR ANALYSIS OF SWIMMING POOL WATER AND ANALYTICAL CELL UTILIZED THEREIN

[75] Inventor: Paul A. Yager, River Edge, N.J.
[73] Assignee: PoolChem, Inc., Passaic, N.J.
[21] Appl. No.: 709,030
[22] Filed: May 31, 1991
[51] Int. Cl.$^5$ .......................................... G01N 27/26
[52] U.S. Cl. .................................... 204/405; 204/433; 204/409; 204/400
[58] Field of Search ................ 204/405, 433, 153.13, 204/153.21, 409, 400, 153.1

[56] References Cited

U.S. PATENT DOCUMENTS

| | | | |
|---|---|---|---|
| 3,761,376 | 9/1973 | Barstow et al. | 204/153.13 |
| 3,846,270 | 11/1974 | Muto et al. | 204/405 |
| 3,950,237 | 4/1976 | Arawa et al. | 204/405 |
| 4,003,705 | 1/1977 | Buzza et al. | 204/405 |
| 4,203,156 | 5/1980 | Ishikawa | 364/500 |
| 4,525,266 | 6/1985 | Schmidt et al. | 204/431 |
| 4,587,003 | 5/1986 | Tantram et al. | 204/431 |
| 4,627,906 | 12/1986 | Gough | 204/415 |

OTHER PUBLICATIONS

Coastal Industries Brochures on "Water Wizard" Pool Water Analyzer.

*Primary Examiner*—John Niebling
*Assistant Examiner*—Bruce F. Bell

[57] ABSTRACT

A swimming pool water analyzer has a housing providing a coulometric titration chamber, a chlorine concentration measuring chamber, a chamber for measuring pH, and conduits connecting the several chambers, the reservoir and a discharge outlet. One or more pumps move fluid through the conduits and chambers to the discharge outlet. Electrodes in each of the chambers are connected to electrical circuitry, and a power supply is provided. A microprocessor receives and analyzes signals indicative of the activity at the electrodes and provides outputs representing values for the chemistry of the sample determined as a result of such analysis of the signals.

29 Claims, 7 Drawing Sheets

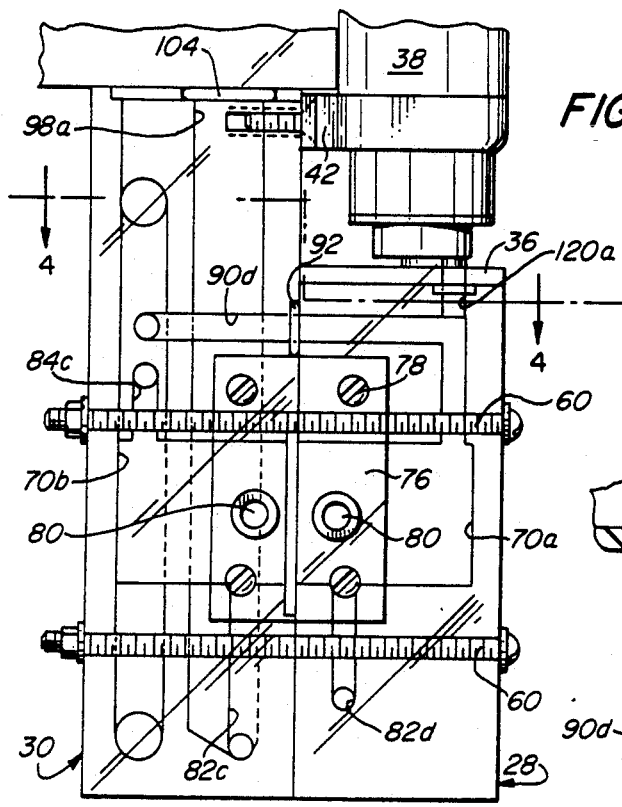
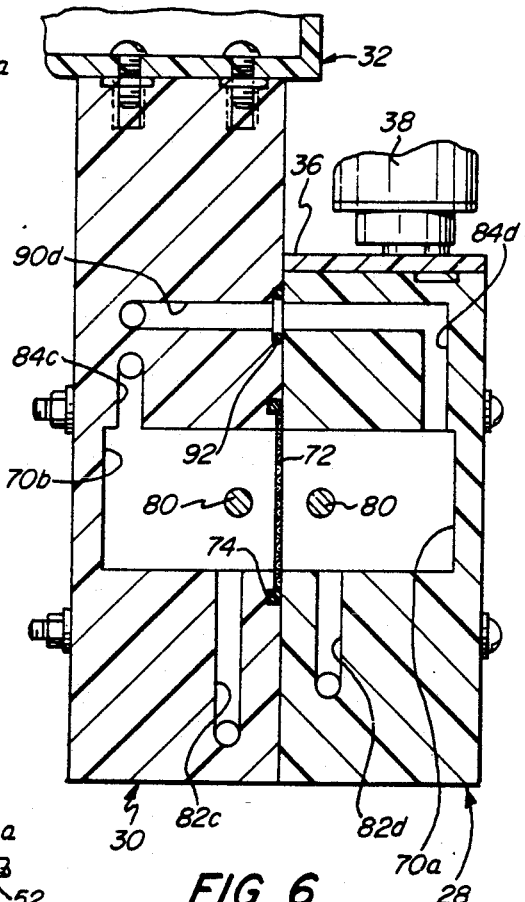
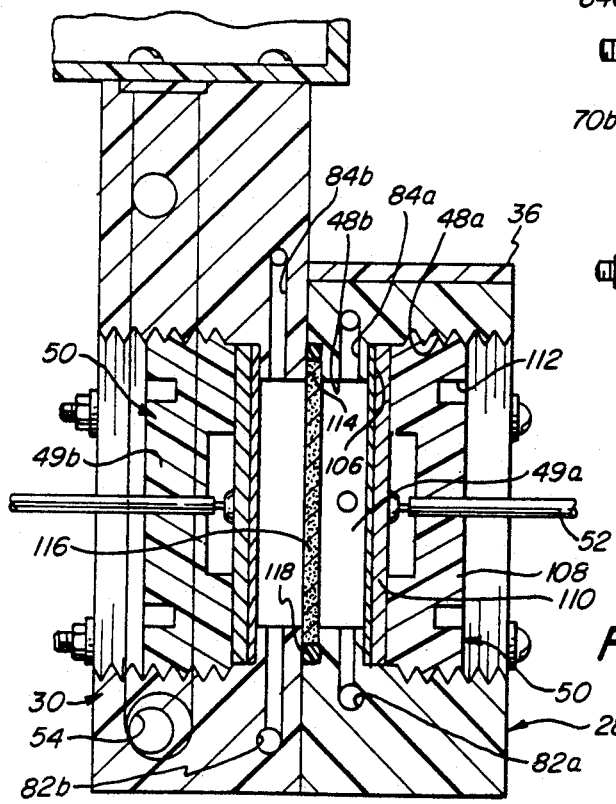
FIG. 5
FIG. 6
FIG. 7

METHOD AND APPARATUS FOR ANALYSIS OF SWIMMING POOL WATER AND ANALYTICAL CELL UTILIZED THEREIN

BACKGROUND OF THE INVENTION

The present invention relates to apparatus for analysis of water and, more particularly, to microprocessor controlled apparatus for concurrently performing a series of electrochemical analyses on a sample of swimming pool water.

It has long been known that it is desirable to balance the chemicals added to swimming pool water in order to control bacteria and algae while avoiding excessive free chlorine and limiting the amount of deviation of the pH from neutral. If this balancing is not done properly, contaminated pool water may cause infections or appear cloudy, or the pool wall may become slimy. If free chlorine level and pH are not controlled, the eyes and skin may be irritated.

As a result, pool owners frequently conduct tests to determine pH and chlorine content and, based upon the measured values, add estimated amounts of pool water treatment chemicals. However, the tests which are generally conducted by a home pool owner are of limited character and are generally insufficient to effect full control over the desired chemistry of the water.

Generally, desirable analyses of swimming pool water would include determinations of all or most of the following: cyanuric acid content, pH, free chlorine, dissolved solids, and total alkalinity. With this information, and information as to the total water volume of the pool, it is possible to calculate the amount of various chemical additions required to balance the chemistry of the pool water.

In the late 1970's, Applicant's assignee introduced a computer controlled apparatus utilizing various reagents to effect coulometric evaluation of swimming pool water samples. The operation and accuracy of this apparatus have been enhanced over the years, but there has been a desire to make analysis faster, less complex and more accurate. Moreover, its use of reagents and test tubes for testing has required restocking of reagents and washing of test tubes.

It is an object of the present invention to provide a novel microprocessor controlled apparatus and method for automatically analyzing swimming pool water samples by electrochemical techniques.

It is also an object to provide such apparatus which is reliable and long-lived, and which is simple to operate.

Another object is to provide such apparatus and method which will provide an output indicating the amounts of various chemicals to be added to the pool water to balance its chemistry.

A further object is to provide such apparatus which is simple to maintain and which is operable without reagents or other chemical additives.

SUMMARY OF THE INVENTION

It has been found that the foregoing and related objects may be readily attained in a swimming pool water analyzer which includes a reservoir for a pool water sample to be analyzed, and a housing providing (i) a chamber for coulometric titration, (ii) a chamber for measuring chlorine concentration, (iii) a chamber for measuring pH, and (iv) conduits connecting the several chambers, the reservoir and a discharge outlet. Electrodes are disposed in each of the chambers for the coulometric titration and the measurements of the sample, and pump means is provided for moving fluid through the conduits and chambers to the discharge outlet. A power supply is provided for the pump means and electrodes, and electrical circuitry is connected to the electrodes and pump means. A microprocessor is included to receive and analyze signals indicating the activity at the electrodes and to provide outputs representing the values for the chemistry of the sample determined as a result of such analysis of the signals.

In the preferred embodiment, the chamber for coulometric titration has a pair of electrodes spaced apart and a membrane therebetween dividing the chamber into two half-cells, and conduits connect the coulometric titration chamber with the pH measurement chamber. A shorting electrode is provided adjacent the pH measurement chamber to isolate this chamber electrically from current flowing in the coulometric titration chamber. The coulometric titration chamber has an inlet conduit thereinto adjacent its lower end from the reservoir and an outlet conduit therefrom adjacent its upper end; the water flowing thereinto expels air therefrom and turbulence therein is minimized.

A temperature sensor is desirably included to transmit to the microprocessor signals indicative of the temperature of the sample. The microprocessor utilizes the titration and pH determination signals to evaluate total alkalinity and cyanuric acid concentration in the sample. The microprocessor also processes the received signals to determine the dissolved solids concentration of the sample. Memory means is included for providing reference values for comparison by the microprocessor with the received signals.

Desirably, the apparatus includes an output device to display the values determined by the microprocessor, and this may be one or both of a printer and a cathode ray tube display.

Preferably, the apparatus includes a control circuit for actuating the pump means to flush the chambers with a sample placed in the reservoir and for providing current to electrodes. A chlorine generating chamber is desirably provided in communication with the chlorine concentration measuring chamber, and electrodes are provided therein for generating free chlorine from a water sample to maintain at least a predetermined amount of free chlorine in the water about the electrode in the chlorine concentration measuring chamber.

The microprocessor desirably also includes means for determining the amount of chemicals to be added to the water from which the sample is taken to bring its chemistry within specified ranges, and the memory means contains reference values for comparison with the signals by the microprocessor to determine the values for the chemistry and the amount of chemicals to be added.

In the method for analyzing the swimming pool water, the operator is able to utilize the apparatus to concurrently conduct coulometric titration, electrochemical determination of free chlorine concentration, and electrochemical measurement of the pH of a water sample, with the coulometric titration and pH measurement being simultaneously conducted with the water sample recirculating therebetween.

The values determined are compared with stored reference values to determine the chemistry of the sample, and the values of pH, free chlorine concentration, and total alkalinity determined for the chemistry of the sample are then displayed.

Preferably, a shorting electrode is provided across the paths of recirculation for the sample to isolate the pH measurement electrically from current flowing in the coulometric titration. The determined values are also compared with reference values to determine cyanuric acid concentration and dissolved solids concentration in the sample.

Desirably, the method includes a terminal step of electrochemically generating free chlorine in the water surrounding the electrode used for the chlorine measurement to maintain this electrode in a ready state for subsequent analysis. The determined values are also used to determine the amount of chemicals to be added to the water from which the sample is taken to bring its chemistry within predetermined ranges.

BRIEF DESCRIPTION OF THE DRAWINGS

FIG. 5 is a fragmentary elevational view of the left end of the apparatus as seen in FIG. 2 with internal portions of the structure shown in full line due to the transparency of the material from which the apparatus is fabricated;

FIG. 6 is a fragmentary sectional view thereof along the line 6—6 of FIG. 4;

FIG. 7 is a fragmentary sectional view thereof along the line 7—7 of FIG. 4;

DETAILED DESCRIPTION OF PREFERRED EMBODIMENT OF THE INVENTION

Figure 8:
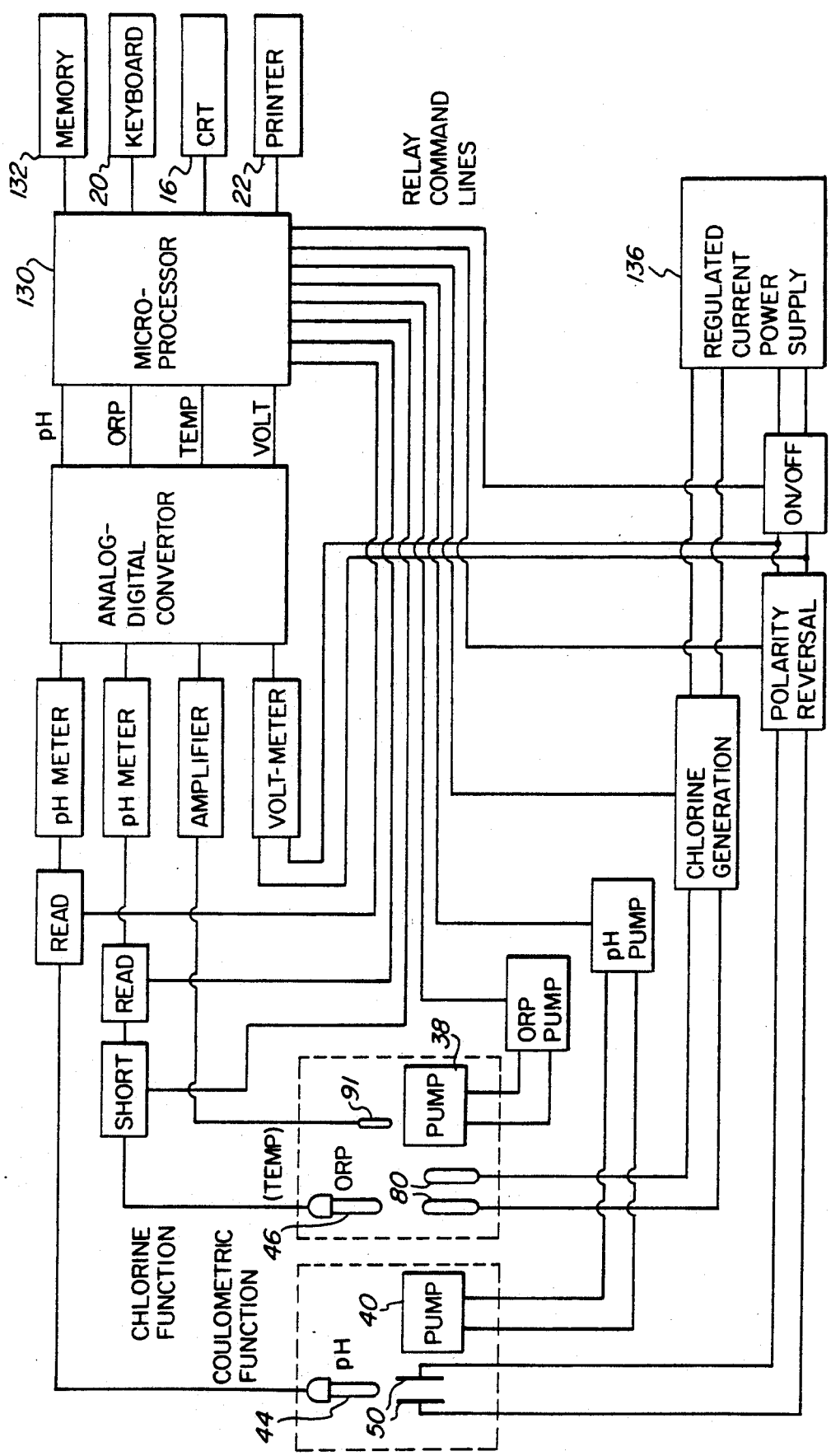
FIG. 8 is a schematic view of the electronic and electrical components of the apparatus.
Figure 9:
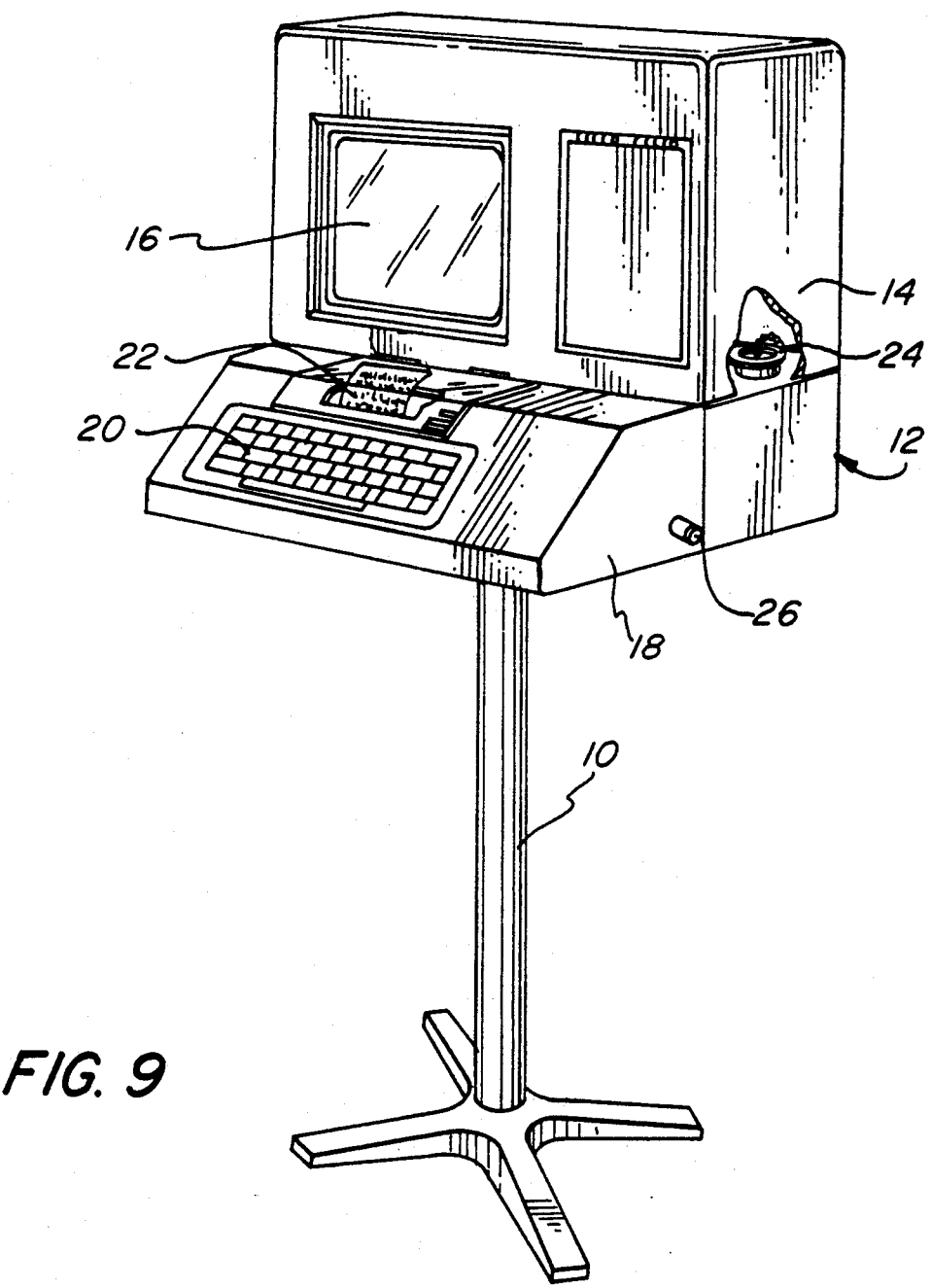
FIG. 9 is a front view of a swimming pool water analyzer embodying the present invention for installation by swimming pool dealers and like facilities.

Turning first to FIG. 9, therein illustrated is a swimming pool water analysis station embodying the present invention comprising a stand 10 and a cabinet generally designated by the numeral 12 supported thereon. The upstanding portion 14 of the cabinet 12 contains a cathode ray tube display screen 16 and electronic and electrical components (seen in FIG. 8). The lower portion 18 of the cabinet 12 has a keyboard 20 and printer 22 seated therein at the front and the analytical cell housing (not shown) behind, and electronic and electrical components (see FIG. 8), with only the fill tube 24 being visible. At the base of the lower portion 18 is a drain tube 26 from the cell housing which discharges into a suitable receptacle (not shown).

Figure 1:
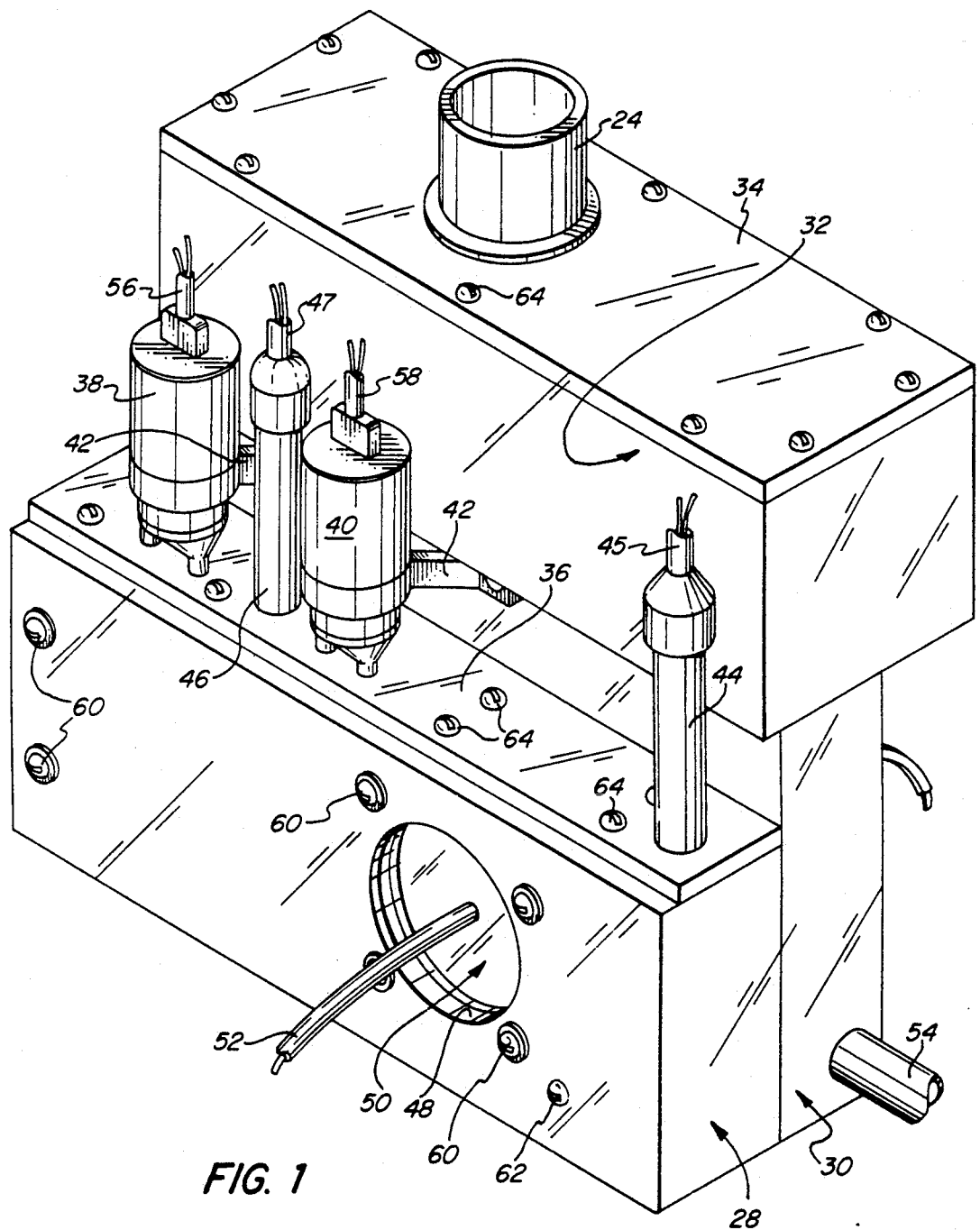
FIG. 1 is a perspective view of an electrochemical cell and reservoir used in apparatus embodying the present invention with various of the electrical and fluid connections omitted or broken away for clarity of illustration.

Turning now to FIG. 1, the analytical cell housing is comprised of a pair of elongated rectangular front and rear sections generally designated by the numerals 28, 30, and the rear section 30 has mounted thereon the rectangular reservoir generally designated by the numeral 32 with a top cover 34 in which is supported the fill tube 24.

The front section 28 has a top plate 36 thereon, and a pair of electrically operated pumps 38, 40 are supported thereon and secured to the rear section 30 by brackets 42. A pH electrode 44 and an ORP electrode 46 are supported on the top plate 36, and have conductors 45, 47 extending therefrom to the electronics (seen in FIG. 8). Threadably seated in an aperture 48 in its front face is an electrode unit generally designated by the numeral 50a and its power cable 52 is fragmentarily illustrated. At the side of the rear section 30 can be seen the outlet fitting 54 to which the drain tube 26 (not shown) is connected. Also shown are the conductors 56, 58 from the pumps 38, 40.

Securing the two sections 28, 30 tightly together are elongated threaded fasteners 60 which extend through solid portions thereof. Also seen is the end of a conductive fastener 62 which acts to electrically isolate the pH electrode 44 as will be described hereinafter. The top cover 34 and top plate 36 are threadably secured to the underlying structure by machine screws 64 to facilitate assembly as well as subsequent disassembly for cleaning and maintenance.

Figure 2:
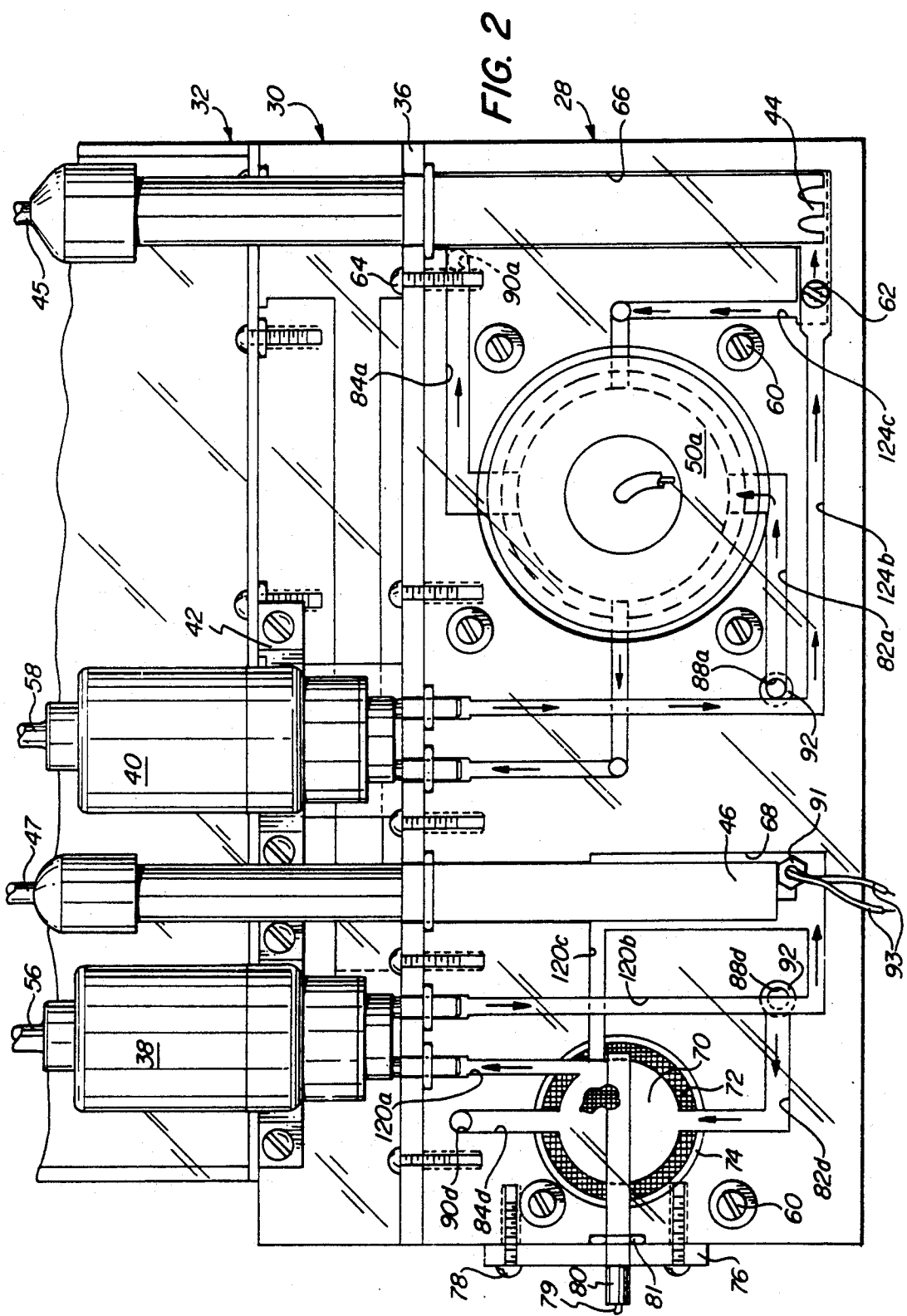
FIG. 2 is a fragmentary front elevational view thereof with conduits, fasteners, and other elements internally of the structure shown in full line due to the transparency of the material from which the apparatus is fabricated.

Turning next to FIG. 2, much of the internal structure of the front section 28 is illustrated in full line since the material of the housing is fabricated from transparent synthetic resin. As can be seen, the pH electrode 44 and ORP electrode 46 both extend vertically in cylindrical chambers 66, 68 respectively. Adjacent the end of the section 28 nearest the ORP electrode 46, there is milled in the inner face thereof a circular chamber 70a, and a membrane 72 extends thereacross and an O-ring 74 extends thereabout to provide a seal thereabout between the opposed faces of the sections 28, 30. A plate 76 is secured to the end face of the section 28 by fasteners 78 and seats therein an electrode 80 which extends into the chamber 70a. A conductor 79 is connected to the electrode, and an O-ring seal 81 is provided about the electrode 80 between the plate 76 and section 28.

A series of fill and discharge conduits 82, 84 extend through the section 28 among the chamber 70a, the electrode chambers 66, 68, the chamber defined by the aperture 48, and the inlet and outlet fittings 86 on the pumps 38, 40. These provide for flow of the water sample to and from the several chambers wherein testing and other action takes place, as will be described hereinafter. In addition, a series of fill and exit passages 88, 90 extend horizontally to the opposite or inner face of the section 28 to communicate with similar passages in the section 30, as will be described hereinafter. O-rings 92 are provided about these passages 88, 90 to effect a seal between the opposed faces of the sections 28, 30. Extending into the ORP electrode chamber 68 adjacent the base of the electrode 46 is a temperature sensor 91 disposed within a threaded fastener, and electrical leads 93 extend therefrom.

Figure 3:
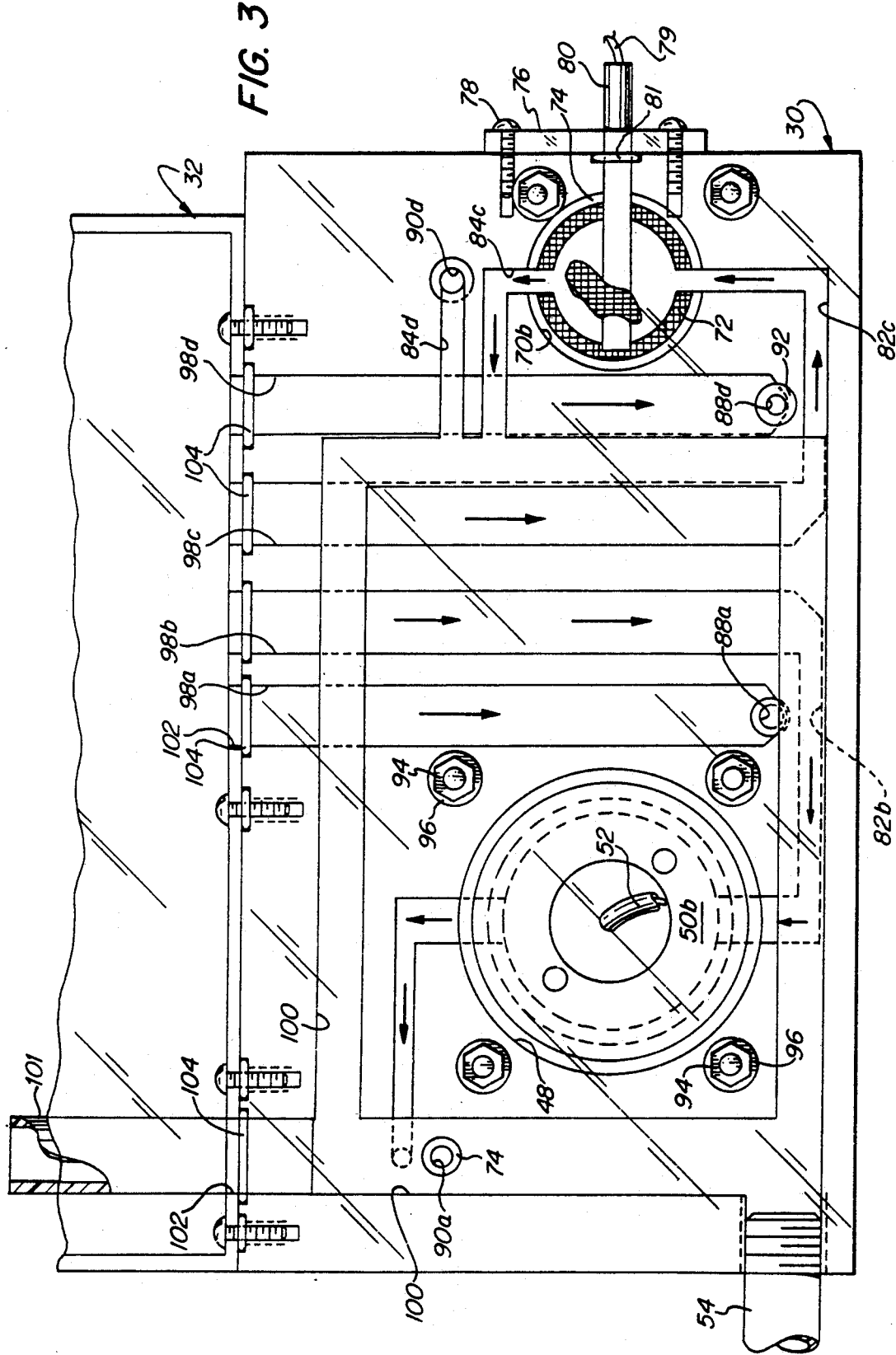
FIG. 3 is a similar fragmentary rear elevational view thereof.
Figure 4:
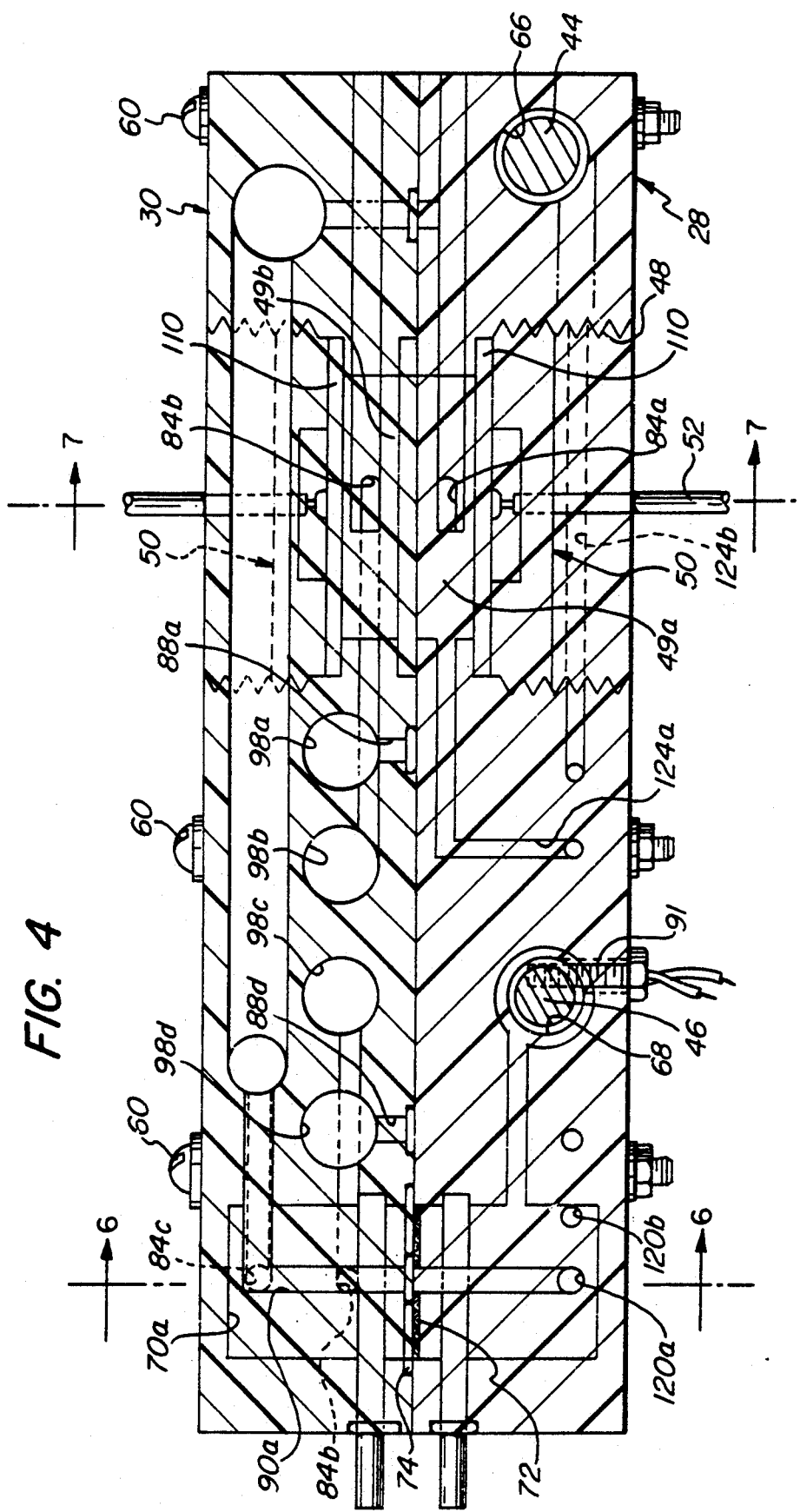
FIG. 4 is a transverse sectional view thereof to an enlarged scale along the line 4—4 of FIG. 5.

Turning next to FIG. 3, the opposite side of the apparatus is therein illustrated, i.e., the outer face of the section 30. Nuts 94 and washers 96 are provided on the fasteners 60 to secure the sections 28, 30 tightly in assembly. As can be seen, the aperture 48 extends therethrough and a second electrode unit 50b is threadably seated therein. Adjacent the one end of the section 30 is a circular chamber 70b milled in its inner face in alignment with the chamber 70a in the section 28, and the plate 76 is similarly secured to the end face of the section 30 and seats an electrode 80 which extends into the chamber 70b.

Four fill passages 98 and a vent/discharge passage 100 extend vertically downwardly from the top face of the section 30 and are aligned with apertures 102 in the base of the reservoir 32. O-rings 104 are provided about the passages 98, 100 between the opposed surfaces of the section 30 and reservoir 32 to effect a seal. A vent tube 101 extends upwardly from the vent/discharge passage 100 to the upper portion of the reservoir 32. A series of conduits 82, 84 are provided among the fill and discharge passages 98, 100, the chambers and the outlet fitting 54. A series of horizontal fill and exit passages 88, 90 extend therefrom to the opposite face and are aligned with those of the section 28.

Turning next to FIG. 6, it can be seen that the two recesses or chambers 70a, 70b provide half-cells which are divided by the membrane 72, and that an electrode 80 extends into each half-cell.

Turning next to FIG. 7, it can be seen that the apertures 48 have an enlarged threaded portion 48a and a reduced diameter portion 48b adjacent the inner or opposed faces of the sections 28, 30, providing a shoulder 106 against which the electrode units 50 seat and seal. As a result, the reduced diameter portions 48b provide aligned chambers 49a and 49b. The electrode units 50a and 50b include a threaded body member 108 and a conductive plate 110 at the inner end thereof, and recesses 112 are provided in the outer face of the body member 108 to seat a spanner wrench or the like to effect its rotation.

Disposed in an annular recess 114 in the inner face of the section 28 about the aperture 48 are a membrane 116 which extends thereacross to create a pair of half-cells and an O-ring 118 to effect a seal between the opposed faces.

In operation of the system, the sample of the swimming pool water is poured into the reservoir 32 through the fill tube 24. The keyboard 20 is utilized to start up the system and the pumps 38, 40 are actuated to cooperate with the gravity flow of water from the reservoir 32 into the cell housing through the fill passages 98 to flush out the remaining water from a prior test.

As can be seen from the drawings, water flows from the reservoir 32 into the fill passage 98d, through the fill passage 88d into the fill conduit 82d, and thence to the chamber 70a. It then flows upwardly therethrough, through the exit conduit 84d, through the exit passage 90d, and thence to the exit conduit 84d in the section 30.

Water flowing from the reservoir 32 through the passage 98c flows through the fill conduit 82c to the chamber 70b and outwardly therefrom through the exit conduit 84c.

When the pump 38 is actuated (and the electrodes 80 are energized), water is drawn from the chamber 70a through the pump conduit 120a and discharged through the pump conduit 120b. It flows into the chamber 68 for the ORP electrode 46 and thence into the return conduit 120c.

Water flowing into the fill passage 98b flows into the fill conduit 82b and into the chamber 49b. It flows outwardly therefrom through the exit conduit 84b to the vent/discharge conduit 100.

Water flowing into the fill passage 98a flows through the fill passage 88a into the fill conduit 82a and thence into the chamber 49a. It flows outwardly from the upper end thereof through the exit conduit 84a and the exit passage 90a into the vent/discharge conduit 100.

As can best be seen in FIG. 2, the pump 40 is connected to the chamber 49a through the pump conduit 124a to withdraw water therefrom and it pumps water through the pump conduit 124b to the bottom of the pH measurement chamber 66 where it passes about the tip of the electrode 44 and thence through the return conduit 124c into the chamber 49a. As seen in FIG. 2, the conductive fastener 62 extends through both conduits 124b and 124c so as to provide a "short" thereacross and electrically isolate the pH electrode 44 from the current flowing in the coulometric titration chambers 49a, 49b.

Turning lastly to FIG. 8, the electronic and electrical components and circuitry of the apparatus are diagrammatically illustrated. The microprocessor 130 accesses memory 132 in response to commands from the keyboard 20, and outputs instructions, and the information concerning its determinations, to either or both of the CRT 16 and printer 22.

The microprocessor 130 also controls relays which are in the circuit from an isolated power supply 136 to the pumps 38, 40 and to the coulometric electrode units 50a, 50b and chlorine generator electrodes 80.

During operation the microprocessor 130 receives output signals from the pH electrode 44, the ORP electrode 46, and the temperature sensor 91, and processes those signals as well as information concerning voltage and time utilized in the coulometric titration.

By comparing data derived from these measurements with reference data stored in the memory 132, the microprocessor 130 determines the chemistry of the sample being analyzed and provides an output to the CRT 16 and/or printer 22 concerning pH, free chlorine concentration, cyanuric acid concentration, total dissolved solids, and total alkalinity.

In the preferred embodiment, the microprocessor 130 also utilizes data entered by the operator to determine the volume of the pool from which the sample was taken, and it utilizes the data concerning the analyses of the sample to provide information concerning the type and amount of chemicals to be added to the water in the swimming pool to bring its chemistry within predetermined ranges.

The cell housing is fabricated from a corrosion resistant and non-conductive material such as synthetic resins and ceramics. Although the body portion thereof can be provided with its passages and chambers by assembling molded sections, blocks are conveniently milled, drilled and machined as required, and undesired lengths of drilled passages may be sealed by resins and plugs. Currently, the housing is being fabricated as illustrated from blocks and plates of polymethyl methacrylate resin which provides transparency to enable inspection and maintenance.

The coulometric titration cell uses a porus ceramic disc as its separator. The disc has a pore size of less than 0.5 micrometers and is manufactured by Cermacon Designs, Ltd. The fineness of the pores prevents the convection flow of liquid from one side of the cell to the other side while permitting the passage of titration current.

The electrodes of the titration cell desirably comprise discs of graphite or EBONEX bonded to brass plates, to which the conductors are attached; EBONEX is a conductive proprietary titanium sub-oxide ceramic sold by Ebonex Technologies, Inc. Both graphite and EBONEX resist corrosion satisfactorily, although EBONEX is preferred for this application.

The current applied to the electrodes of the coulometric cell will normally be on the order of 70-100 milliamperes at a voltage of 30-150 volts for a period of 1-4 minutes.

The membrane utilized in the chlorine generation cell is a composite of a fluorinated polymer film on a synthetic resin fabric. The membrane material is sold by E.I. DuPont under the designation NAFION, and was developed by DuPont for chlorine electrolysis cells.

The electrodes on either side of the chlorine generation cell are rods of EBONEX, which is preferred because it does not consume the chlorine generated, as do electrodes of many other materials.

The current applied to the electrodes of the chlorine generation cell will be on the order of 70-100 milliamps at a voltage of 30-150 volts. The duration of this current flow depends on the concentration of chloride ions in the water.

The concepts involved in the several electrochemical determinations used in the apparatus are described hereinafter.

Titration Function

Hydrogen ions are generated at the positive electrode of the coulometric titration chamber by the reaction $H_2O = \frac{1}{2}O_2 + 2H + 2e^-$.

Hydroxyl ions are generated at the negative electrode of the titration chamber by the reaction $2e^- + 2H_2O = H_2 + 2OH^-$.

Dividing the chamber into halves by the membrane prevents the recombination of the ions allowing them to accumulate.

The hydrogen ions combine with conjugate base species present in the sample and convert them to their corresponding conjugate acid species; this lowers the pH in that half of the chamber where the hydrogen ions accumulate.

The hydroxyl ions combine with the hydrogen ions from conjugate acid species present in the sample and convert the conjugate acid species to their corresponding conjugate base species. This raises the pH in that half of the chamber where the hydroxyl ions accumulate.

The extent to which the pH changes in a given volume of sample depends on the quantity of hydrogen or hydroxyl ions which is generated, and inversely upon the quantity of conjugate base or conjugate acid species initially present.

If the amount of pH change is fixed, then the amount of current required to change it by the given amount depends upon the quantity of conjugate acid or conjugate base initially present. The quantity of these species present can thus be determined from the amount of current required to convert them.

In the present invention, the titration cell or chamber consists of two electrodes of broad area and relatively small spatial separation to allow a high current flow through the sample and consequently a short titration time.

The membrane is a rigid separator of tightly porous material to allow ionic electrical conduction but to limit liquid convection. It maintains the half-cell volumes constant and thus prevents the quantities of liquids they contain from changing with time.

Although pH changes occur in both halves of the cell, for reasons of economical construction, the pH change in only one of the halves is monitored.

The monitoring mechanism consists of the pH electrode over which is circulated liquid from the cell half being observed. The circulation process is provided by the small high flow-rate pump drawing liquid from the half-cell and forcing it over the bulb of the pH electrode, after which it returns to the half-cell.

All of the circulation channels are short to limit the quantity of water which they contain compared with the volume of the half-cell. This limited volume, combined with the high volume pump, produces a turn over rate in the half-cell of several times per second, thus facilitating mixing and approaching a condition during titration, of homogenous, quasi-static pH change. This high turn over rate also allows real time readings of the pH by the pH electrode.

The use of a pump and channels for mixing allows the placement of the pH electrode in a cavity separate from that of the half-cell. This limits the interference of the titration current with the operation of the pH electrode.

Moreover, the interference of the titration current with the operation of the pH electrode is reduced by the fastener which passes perpendicularly through the channels carrying the liquid to and from the pH electrode chamber. This shorts out any electrical field from the coulometric half-cell passing to the pH electrode chamber through the channels.

In addition, an isolated source is used for the electrolytic current fed to the electrodes of the coulometric cell. Under these conditions, substantial voltages applied to the cell plates will not affect the output of the pH electrode. Thus, the pH can be read with the electrolytic current continuously flowing to accelerate the analysis.

This electrolytic current is supplied by a constant current source, which allows solutions of widely varying conductivity to be titrated. The use of a constant current source also simplifies the computation of charge required to produce the pH change.

In operation of the apparatus, with the pump operating, the application of positive current to the monitored half-cell causes the pH of the sample to drop and the application of negative current to the other half-cell causes its pH to rise. The liquid to be tested is brought to the beginning of the pH range by manipulation of the current. The liquid is made to pass through the pH range with the pH, the elapsed time, and the electrolytic current being monitored. The data is fed to the microprocessor which calculates the quantities and identifies the titratable components.

Conductivity

Since a constant current source is being used to provide the titration current, the conductivity of the solution manifests itself as a voltage drop across the cell electrode. Independently of the titration parameters, the voltage drop can be monitored to show the conductivity of the solution. If it is desired, alternating current can be momentarily applied across the electrodes before titration.

Free Chlorine

Elemental chlorine in aqueous solution develops a voltage on a piece of platinum by several reactions:

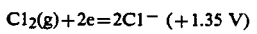

$Cl_2(g) + 2e = 2Cl^-$ (+1.35 V)

$HClO^- + H^+ + 2e = Cl + H_2O$ (+1.49 V)

$$ClO^- + H_2O + 2e = Cl + 2OH \quad (+0.90 \text{ V})$$

The exact voltage varies with the concentration of the chlorine and with the pH of the solution. The platinum is mounted on a shaft along with a KCl solution reference function to form an electrochemical probe, and its voltage output is a function of the solution to which it is exposed.

Using an ORP electrode, the solution to be measured is forced over the platinum tip and the reference function by the small high speed pump, and the tip is allowed to come into equilibrium with the solution, after which the voltage is read.

Because an ORP electrode is very slow to reach equilibrium with a weak chlorine solution, a drastic but effective method of accelerating the attainment of equilibrium is to briefly short the platinum tip with the reference function through the probe leads. This can be a brief direct shorting of zero resistance or it can be the brief placement of substantial resistance, the effect of which is to drop the output of the ORP to a controlled millivolt value above zero millivolts. Residual chlorine on the platinum tip is converted to chloride ion; following this, the probe is irrigated by the pump and the rise to equilibrium in the weaker solution is observed.

An ORP electrode is slow to reach equilibrium after prolonged storage in the absence of chlorine. To prevent this, the measuring apparatus has a chlorine generating cell to generate small amounts of elemental chlorine in the storage solution via electrolysis: $2e + 2Cl^- (+1.35 \text{ V}) = Cl_2$.

Between tests, the apparatus periodically runs the pump and reads the output of the ORP electrode. If the output falls below a preset minimum, a current of electricity is briefly passed through the electrolytic cell. The side of the electrolytic cell in the pump circuit receives positive current, withdrawing electrons from chloride ions, to produce elemental chlorine. The chlorine is then circulated over the ORP electrode by the pump.

The microprocessor is desirably programmed to lead the operator through the sequence of steps necessary to conduct the analyses and display the results. In the embodiment currently being marketed by Applicants assignee, the following sequence of steps are to be found in the operator manual and describe the procedure.

Step 12. Press the "CONTROL" and "S" keys simultaneously. The screen will now tell you to pour the customer's sample water into the reservoir and press the "SPACE BAR".

Step 13. You will now be requested to complete the following information:

---

(Press RETURN)     Customer's Phone No.

(Press RETURN)     Customer's Name (Press RETURN)     Customer's Address (Press RETURN)     City, State, Zip Code

---

When complete the computer will again ask:
IS THE ABOVE INFORMATION CORRECT? (Y/N)

Once you have pressed "Y", the computer will require a number of questions to be answered to insure the accuracy of test results.

Step 14. You will be asked to:
ENTER POOL SIZE IN GALLONS
If the customer does not know the pool gallonage, Press the "N" key and the computer will ask:
SHAPE OF POOL
(A) Round (B) Oval (C) Rectangular
When you choose "A", "B" or "C" the screen will highlight the proper shape pool and you will be asked . . . if the pool is round . . . to:
ENTER DIAMETER (in feet)
(Press RETURN)
ENTER AVERAGE DEPTH (in feet)
(Press RETURN)
If the pool is oval or rectangular, you will be asked to:
ENTER LENGTH (in feet)
(Press RETURN)
ENTER WIDTH (in feet)
(Press RETURN)
ENTER AVERAGE DEPTH (in feet)
(Press RETURN)
If you do not complete the data relating to pool size, the computer cannot continue the program.
After you have finished entering this information, the computer will ask:
IS THE ABOVE INFORMATION CORRECT? (Y/N)

Step 15. Again, after you have pressed the "Y" key, the screen will change and you will be asked to enter the following data:
WHICH OF THE FOLLOWING BEST DESCRIBES YOUR POOL?
(a) VINYL LINED
(b) FIBERGLASS
(c) CONCRETE
One selection must be made. The computer then asks:
WHAT TYPE OF FILTER DOES YOUR POOL HAVE?
(a) SAND (b) DIATOMACEOUS EARTH (c) CARTRIDGE
Again one selection must be made. The computer continues:
WHICH BEST DESCRIBES THE CONDITION OF YOUR POOL WATER?
(a) CRYSTAL CLEAR
(b) CLEAR WITH GREENISH TINT
(c) CLEAR WITH REDDISH BROWN TINT
(d) CLOUDY
(e) CLOUDY WITH GREENISH TINT
(f) CLOUDY WITH REDDISH BROWN TINT
One selection must be made. Next the computer will ask:
ARE POOL WALLS AND STEPS SLIPPERY? (Y/N)
You must press "Y" or "N".
IS THERE SEDIMENT IN YOUR POOL? (Y/N)
Press "Y" or "N".
ARE POOL WALLS AND STEPS STAINED RUST, BLACK OR BROWN? (Y/N)
Press "Y" or "N". Again, the computer will ask:
IS THE ABOVE INFORMATION CORRECT? (Y/N)
NOTE: IF YOU ANSWER "N" ON ANY SCREEN THAT ASKS "IS THE ABOVE INFORMATION CORRECT? (Y/N)" YOU HAVE THE OPPORTUNITY TO CHANGE YOUR ANSWER TO ANY OF THE QUESTIONS ANSWERED.

USE OF THE "ESCAPE" AND "DELETE" KEYS

DELETE KEY: The DELETE key acts much the same as a backspacer on a typewriter. It will erase one character at a time so typing errors may be corrected immediately.

ESCAPE KEY: The ESCAPE key will retreat, when pressed, to the line just prior to the one on which you are working. If that line happens to be the first line on the screen, the ESCAPE key will move the screen back to the one just prior to the screen you are working on.

When the tests are complete the screen will automatically change and you will see the results of each of the tests as they are reported on the screen as well as in the printout. The screen is split. On the left there is an animated bar graph which shows the ideal and less than ideal range for each test. The bar rises until it finds the level indicated by test results. That result is reported on the right section of the screen and remains there until all the tests are complete. Test results will appear in the following order:

TEMPERATURE
CHLORINE
pH
TOTAL ALKALINITY
CHLORINE STABILIZER
TOTAL DISSOLVED SOLIDS

In addition, the printer will produce a printout containing the customer information, the test results, and the recommended dosages and notes on proper pool maintenance.

When the printout is complete the computer will ask:
WOULD YOU LIKE ANOTHER PRINTOUT? (Y/N)

If you answer "N", the screen returns to the beginning of the program at Step No. 12. Press "CONTROL" and "S" once again and you are ready for your next customer.

Thus, it can be seen from the foregoing detailed specification and drawings that the apparatus and method of the present invention enable rapid and accurate analysis of a swimming pool water sample to determine key factors in its chemistry and the amount and nature of chemical additives to be made to balance the chemistry in the swimming pool. The apparatus is relatively simple to operate and maintain and does not require reagents or test tubes.

Having thus described the invention, what is claimed is:

1. A swimming pool water analyzer comprising:
   (a) a reservoir for a pool water sample to be analyzed;
   (b) a housing providing (i) a chamber for coulometric titration, (ii) a chamber for measuring chlorine concentration, (iii) a chamber for measuring pH, and (iv) conduits connecting said several chambers, said reservoir and a discharge outlet;
   (c) electrodes in each of said chambers for said coulometric titration and measurements of a sample;
   (d) pump means for moving fluid through said conduits and chambers to said discharge outlet;
   (e) power supply means for said pump means and electrodes;
   (f) electrical circuitry connected to said electrodes and pump means; and
   (g) means electrically isolating said coulometric titration and pH measurement chambers;
   (h) a microprocessor for receiving and analyzing signals indicating the activity at said electrodes and for providing outputs representing the values for the chemistry of the sample determined as a result of such analysis of the signals.

2. The swimming pool water analyzer in accordance with claim 1 wherein said chamber for coulometric titration has a pair of electrodes spaced apart and a membrane therebetween dividing said chamber into two half-cells and wherein conduits connect said coulometric titration chamber with said pH measurement chamber.

3. The swimming pool water analyzer in accordance with claim 2 wherein said electrical isolation means is a shorting electrode provided across the conduits adjacent said pH measurement chamber to isolate said pH measurement chamber electrically from current flowing in said coulometric titration chamber.

4. The swimming pool water analyzer in accordance with claim 1 wherein said coulometric titration chamber has an inlet conduit thereinto adjacent its lower end from said reservoir and an outlet conduit therefrom adjacent its upper end, whereby sample flow thereinto expels air therefrom and turbulence therein is minimized.

5. The swimming pool water analyzer in accordance with claim 1 wherein there is included a temperature sensor for transmitting to said microprocessor signals indicative of the temperature of the sample.

6. The swimming pool water analyzer in accordance with claim 1 wherein said microprocessor utilizes said titration and pH determination signals to evaluate total alkalinity and cyanuric acid concentration in the sample.

7. The swimming pool water analyzer in accordance with claim 6 wherein said microprocessor processes the received signals to determine the dissolved solids concentration of the sample.

8. The swimming pool water analyzer in accordance with claim 1 wherein there is included memory means for providing reference values for comparison by said microprocessor with said received signals.

9. The swimming pool water analyzer in accordance with claim 1 wherein said apparatus includes an output device to display the values determined by said microprocessor.

10. The swimming pool water analyzer in accordance with claim 9 wherein said output device is a printer.

11. The swimming pool water analyzer in accordance with claim 9 wherein said output device is a cathode ray tube display.

12. The swimming pool water analyzer in accordance with claim 1 wherein said apparatus includes a control circuit for actuating said pump means to flush said chambers with a sample placed in said reservoir and for providing current to said electrodes.

13. The swimming pool water analyzer in accordance with claim 1 wherein there is included a chlorine generating chamber in communication with said chlorine concentration measuring chamber and electrodes therein for generating free chlorine from a water sample to maintain free chlorine in the water about said electrode in said chlorine concentration measuring chamber.

14. The swimming pool water analyzer in accordance with claim 1 wherein said microprocessor includes means for determining the amount of chemicals to be added to the water from which the sample is taken to bring its chemistry within specified ranges.

15. The swimming pool water analyzer in accordance with claim 14 wherein there is included memory means containing reference values for comparison with said signals by said microprocessor to determine the values for the chemistry and the amount of chemicals to be added.

16. The swimming pool water analyzer in accordance with claim 14 wherein said apparatus includes an output device to display the values determined by said microprocessor.

17. The swimming pool water analyzer in accordance with claim 14 wherein said output device is a printer.

18. The swimming pool water analyzer in accordance with claim 2 wherein said pump means and conduits cooperate to circulate the sample through conduits between said coulometric titration chamber and pH measurement chamber.

19. A swimming pool water analyzer comprising:
(a) a reservoir for a pool water sample to be analyzed;
(b) a housing providing (i) a chamber for coulometric titration, (ii) a chamber for measuring chlorine concentration, (iii) a chamber for measuring pH, and (iv) conduits connecting said several chambers, said reservoir and a discharge outlet, said coulometric titration chamber having a pair of electrodes spaced apart and a membrane therebetween dividing said chamber into two half-cells, said coulometric titration chamber being connected with said pH measurement chamber by conduits;
(c) electrodes in each of said chambers for said coulometric titration and measurements of a sample;
(d) pump means for moving fluid through said conduits and chambers to said discharge outlet;
(e) power supply means for said pump means and electrodes;
(f) electrical circuitry connected to said electrodes and pump means;
(g) means electrically isolating said coulometric titration and pH measurement chambers;
(h) a microprocessor for receiving and analyzing signals indicating the activity at said electrodes and for providing outputs representing the values for the chemistry of the sample determined as a result of such analysis of the signals;
(i) memory means for providing reference values for comparison by said microprocessor with said received signals; and
(j) an output device to display the values determined by said microprocessor.

20. The swimming pool water analyzer in accordance with claim 19 wherein said electrical isolation means is a shorting electrode provided across the conduits adjacent said pH measurement chamber to isolate said pH measurement chamber electrically from current flowing in said coulometric titration chamber.

21. The swimming pool water analyzer in accordance with claim 19 wherein said pump means and conduits cooperate to circulate the sample through conduits between said coulometric titration chamber and pH measurement chamber.

22. The swimming pool water analyzer in accordance with claim 21 wherein said coulometric titration chamber has an inlet conduit thereinto adjacent its lower end from said reservoir and an outlet conduit therefrom adjacent its upper end, whereby sample flow thereinto expels air therefrom and turbulence therein is minimized.

23. The swimming pool water analyzer in accordance with claim 19 wherein said microprocessor utilizes said titration and pH determination signals to evaluate total alkalinity and cyanuric acid concentration in the sample, and also processes the received signals to determine the dissolved solids concentration of the sample.

24. The swimming pool water analyzer in accordance with claim 19 wherein said apparatus includes a control circuit for actuating said pump means to flush said chambers with a sample placed in said reservoir and for providing current to said electrodes.

25. The swimming pool water analyzer in accordance with claim 19 wherein there is included a chlorine generating chamber in communication with said chlorine concentration measuring chamber and electrodes therein for generating free chlorine from a water sample to maintain free chlorine in the water about said electrode in said chlorine concentration measuring chamber.

26. The swimming pool water analyzer in accordance with claim 19 wherein said microprocessor includes means for determining the amount of chemicals to be added to the water from which the sample is taken to bring its chemistry within specified ranges, and wherein said memory means containing reference values for comparison with said signals by said microprocessor to determine the amount of chemicals to be added.

27. In an analytical apparatus for aqueous samples the combination comprising:
(a) a housing providing (i) a chamber for coulometric titration, (ii) a chamber for measuring pH, and (iii) conduits connecting said chambers;
(b) a pair of electrodes spaced apart in said coulometric titration chamber and a membrane therebetween dividing said chamber into two half-cells said conduits connecting one half-cell of said coulometric titration chamber with said pH measuring chamber;
(c) pump means for moving fluid through said conduits and chambers;
(d) means electrically isolating said coulometric titration and pH measurement chambers.

28. The analytical apparatus in accordance with claim 27 including a microprocessor for receiving and analyzing signals indicating the activity at said electrodes and for providing an output representing the value for the chemistry of the sample determined as a result of such analysis of the signals.

29. The analytical apparatus in accordance with claim 28 wherein said electrical isolation means is a shorting electrode provided across the conduits adjacent said pH measurement chamber to isolate said pH measurement chamber electrically from current flowing in said coulometric titration chamber.

* * * * *